United States Patent [19]

Hurni et al.

[11] 4,004,981
[45] Jan. 25, 1977

[54] CELL REMOVING DEVICE

[75] Inventors: William M. Hurni, North Wales; William J. McAleer, Ambler; Maurice R. Hilleman, Lafayette Hill, all of Pa.

[73] Assignee: Merck & Co., Inc., Rahway, N.J.

[22] Filed: May 1, 1975

[21] Appl. No.: 573,655

[52] U.S. Cl. .................. 195/127; 195/1.7; 15/236 R
[51] Int. Cl.² .................. C12K 9/00; C12K 1/10
[58] Field of Search ........... 195/127, 1.7; 128/304; 15/236 R, 188, 186

[56] References Cited
UNITED STATES PATENTS

| | | | |
|---|---|---|---|
| 289,550 | 12/1883 | Miles | 15/142 |
| 503,661 | 8/1893 | Gnuchtel | 15/186 |
| 1,085,063 | 1/1914 | Prouty et al. | 15/236 R |
| 1,734,429 | 11/1929 | Hanover | 15/186 |
| 1,916,842 | 7/1933 | Lander | 15/236 R |
| 2,291,015 | 7/1942 | Anderson | 15/236 R |
| 2,637,870 | 5/1953 | Cohen | 15/188 |
| 3,540,700 | 11/1970 | Freedman | 195/127 |

OTHER PUBLICATIONS

Parker, *Methods of Tissue Culture* Harper & Row Publishers pp. 187 & 188 (1961).

*Primary Examiner*—Alvin E. Tanenholtz
*Attorney, Agent, or Firm*—Donald J. Perrella; J. Jerome Behan

[57] ABSTRACT

Apparatus for physically removing cells in sterile manner from a disc stack on which the cells have been cultured comprises a substantially shaft-like member having at least one rod-like member mounted at substantially a right angle to the axis of the shaft.

9 Claims, 4 Drawing Figures

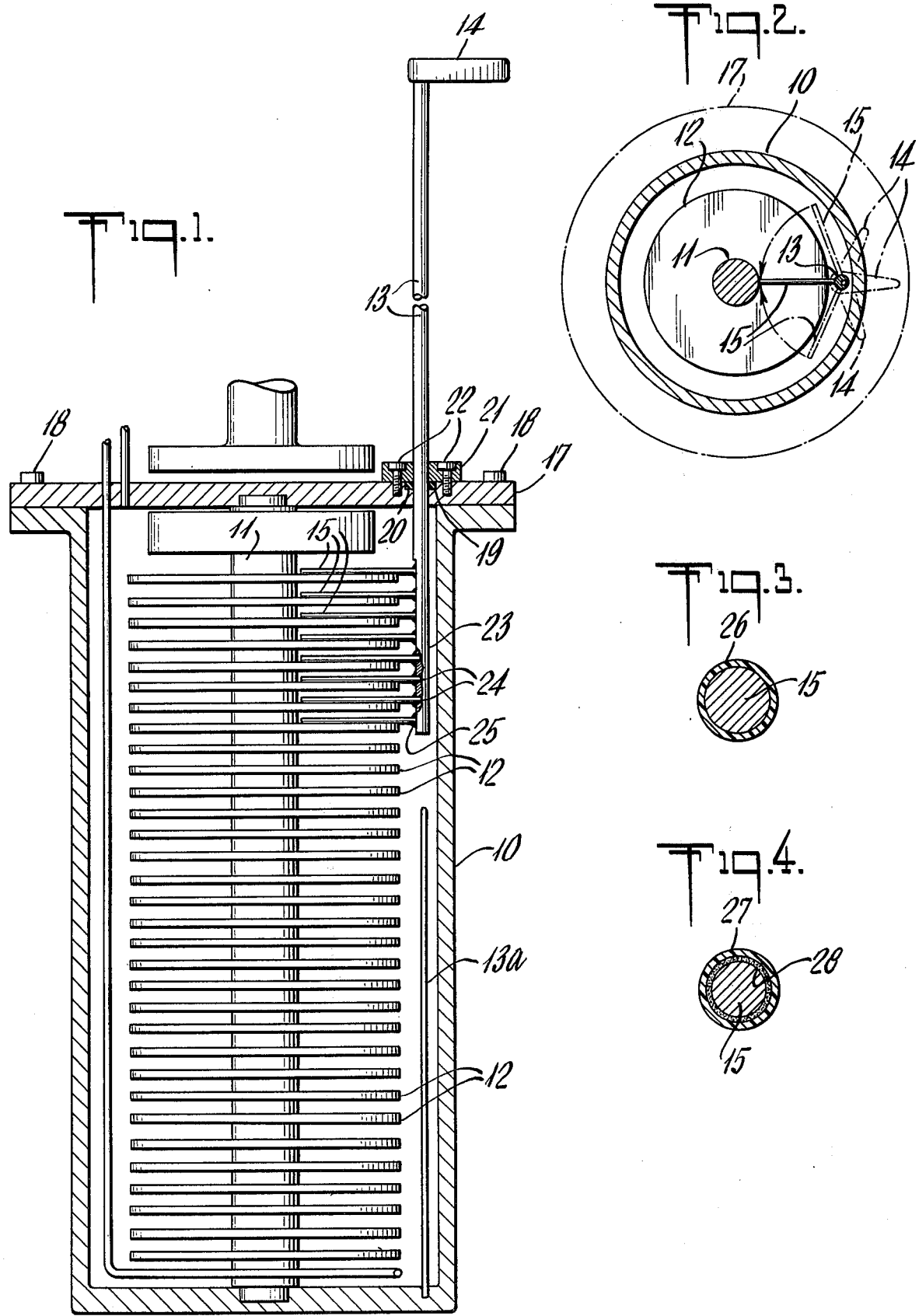

CELL REMOVING DEVICE

BACKGROUND OF THE INVENTION

The present invention relates to apparatus for removing cells and, more particularly, to apparatus for physically removing cells in sterile manner from a disc stack on which cells are cultured in a mass cell culture apparatus.

Systems have been developed for the mass culture of cells such as, for example, the multi-plate system disclosed in U.S. Pat. No. 3,407,120 and the Biotech cylindrical rotating disc apparatus. A major difficulty associated with the use of such mass culture systems, however, is that of removing the cells from the discs on which they have been cultured. Prior art method of removing the cells involve the use of enzymes, such as trypsin which have the disadvantage of causing, to some extent at least, undesired chemical degradation of the cells.

It is, accordingly, an object of the present invention to provide apparatus and method for physically removing cells in a sterile manner from mass cell culture apparatus. Another object of the present invention is to provide an apparatus and method for physically removing cells in sterile manner from the discs of the multi-plate or multi-disc mass cell culture apparatus. These and other objects will be apparent from the following detailed description.

SUMMARY OF THE INVENTION

Apparatus for physically removing cells in sterile manner from a disc stack on which the cells have been cultured comprises a substantially shaft-like member having at least one rod-like member mounted at substantially a right angle to the axis of the shaft. The rod-like member may be provided with a flexible, substantially inert, impermeable material.

BRIEF DESCRIPTION OF THE DRAWINGS

FIG. 1 is a sectional view of a multi-plate cell culture apparatus fitted with a cell removing device of the present invention;

FIG. 2 is a plan view of the apparatus of FIG. 1;

FIGS. 3 and 4 are sectional views of various rod-like members.

DETAILED DESCRIPTION

Referring now to the drawings, FIG. 1 is a sectional view of a known rotating disc apparatus described in U.S. Pat. No. 3,839,155 whose disclosure is hereby incorporated by reference. The apparatus is equipped with a cell removing device according to the present invention preferably formed of a metal suitable for cell culture conditions, e.g., stainless steel or titanium. The apparatus comprises a cylindrical shell 10 having a central shaft 11 on which are mounted a plurality of discs 12 on whose surfaces the cells are cultured. Also fixedly mounted on the shaft is a magnetic couple (not shown) which is engaged by external magnetic drive means (not shown) in order to rotate the discs 12. The cell removing device consists of a substantially shaft-like member 13 having a turning handle 14 at its uppermost end and a plurality of rod-like members 15, each of which is attached at about a right angle to a portion of the shaft. The shaft is of such length that member 15 which is furthest from the handle can contact the disc 12 which is furthest from the handle. Members 15 are spaced apart from one another so as to fit between adjacent discs to contact the lower surface of a disc closer to the handle and the upper surface of the adjacent disc further from the handle, as well as to contact the upper surface of the disc closest to the handle and the bottom surface of the disc furthest from the handle. The shaft 13 passes through a circular opening 16 in the cover plate 17 which is secured to the top of the apparatus by bolts 18. The shaft 13 is hollow and thereby adapted to fit over guide rod 13a which is fixed to the bottom plate of the shell.

A recessed flange 19 in the upper surface of opening 16 is adapted to receive an O-ring 20 which is covered with a cap 21 which is fixed to plate 17 by screws 22 to seal opening 16.

The lower portion of shaft 13 has a flat surface 23 having a plurality of recesses 24, each recess adapted to receive a rod-like member 15. Members 15 may be secured in recesses 24 by soldering, or both the recesses 24 and the ends of the members 15 may be threaded so that the members 15 may be screwed into recesses 24, or by other suitable means. If attached by soldering, a solder fillet 25 is provided at the flat surface 23 to strengthen the attachment.

FIG. 2 is a plan view of the rotating disc apparatus with plate 17 removed and showing cylindrical shell 10, central shaft 11 and top disc 12, turning handle 14 and top rod-like member 15. By turning handle 14, shaft 13 is rotated thereby sweeping rod-like member 15 across the surface of disc 12 and displacing cells from the surface of disc 12 into the liquid medium in the apparatus from which liquid medium and cells are drawn off. Alternatively, shaft 13 may be turned to engage members 15 and disc 12 and shaft 11 rotated to turn discs 12.

FIG. 3 is a cross section of a rod-like member 15 having a coating 26 thereon of a flexible, substantially inert, impermeable material which is able to withstand steam sterilization such as polyfluorinated hydrocarbon, e.g., Teflon. The properties of Teflon are summarized in the 1953 edition of Handbook of Material Trade Names, p. 558.

FIG. 4 is a cross section of another rod-like member 15 surrounded by tubing 27 with the space between the tubing 27 and member 15 filled with a flexible adhesive 28 which is able to withstand steam sterilization such as a silicone rubber.

The plain rod-like member without coating or tubing is obvious and not shown in the drawings.

When used with a multi-plate cell culture apparatus, the cell removing apparatus of the present invention is positioned against the inside wall of shell 10 by turning handle 14. When the cell culture operation is completed, the handle 14 is turned causing shaft 13 to rotate and causing rod-like member 15 to sweep in arcuate manner across the surface of disc 12 displacing cells it meets and pushing off the edge of the disc into the liquid medium in the cell culture apparatus. The shaft 11 on which the disc is mounted is then partially rotated, e.g. about 90°, bringing another cell coated portion of disc 12 within the area swept by member 15. About 3 or 4 partial rotations of shaft 11 are sufficient to enable member 15 to displace substantially all of the cells on disc 12. Member 15 may then be turned against the inner wall of shell 10 and raised or lowered to contact another disc. Alternatively, the handle may be turned to bring the rod-like member 15 in contact with at least part of a surface of a disc and shaft 11 rotated by the magnetic drive means to displace cells.

What is claimed is:

1. In a multiplate cell propagator comprising a substantially cylindrical vessel having a plurality of spaced apart parallel discs on which cells are grown, the discs mounted on a rotatable shaft within the vessel, the improvement comprising a second shaft pivotably mounted within the vessel, the second shaft having mounted thereon parallel to the plane of the discs a contacting means adapted to contact at least part of the surface of a disc upon pivotal movement of the second shaft whereby cells are removed from the surface of the disc, the contacting means comprising a substantially rod-like member.

2. Apparatus according to claim 1 wherein the rod-like member is coated with a flexible, substantially inert, impermeable material.

3. Apparatus according to claim 1 wherein the rod-like member is covered with a tubing of flexible, substantially inert, impermeable material bonded to the rod-like member by a flexible adhesive.

4. Apparatus according to claim 3 wherein the tubing is polyfluorinated hydrocarbon.

5. Apparatus according to claim 1 wherein the second shaft has a substantially flat surface from which the substantially rod-like member is mounted.

6. Apparatus according to claim 5 wherein the rod-like member is mounted in a recess provided in the substantially flat surface.

7. Apparatus according to claim 5 wherein the second shaft has a hollow portion adapted to be fitted over a guide rod.

8. Apparatus according to claim 5 having a plurality of substantially rod-like members.

9. A method for physically removing cells from a plurality of discs mounted on a central shaft on which discs the cells have been cultured comprising the steps of positioning apparatus according to claim 1 so that the substantially rod-like member is between adjacent discs and rotating the second shaft so that the rod-like member contacts at least part of the surface of an adjacent disc.

* * * * *